United States Patent
Jung et al.

(10) Patent No.: US 9,939,368 B2
(45) Date of Patent: Apr. 10, 2018

(54) PHOTOACOUSTIC APPARATUS AND METHOD OF OPERATING THE SAME

(71) Applicants: SAMSUNG MEDISON CO., LTD., Hongcheon-gun, Gangwon-Do (KR); SAMSUNG ELECTRONICS CO., LTD., Suwon-si, Gyeonggi-do (KR)

(72) Inventors: Jong-kyu Jung, Gangwon-do (KR); Dal-kwon Koh, Gangwon-do (KR); Jung-ho Kim, Gangwon-do (KR); Jung-taek Oh, Seoul (KR); Jae-kwang Lee, Gyeonggi-do (KR)

(73) Assignees: Samsung Medison Co., Ltd., Hongcheon-gun, Gangwon-do (KR); Samsung Electronics Co., Ltd., Suwon-si, Gyeonggi-do (KR)

( * ) Notice: Subject to any disclaimer, the term of this patent is extended or adjusted under 35 U.S.C. 154(b) by 530 days.

(21) Appl. No.: 14/490,558

(22) Filed: Sep. 18, 2014

(65) Prior Publication Data
US 2015/0122032 A1    May 7, 2015

(30) Foreign Application Priority Data
Nov. 1, 2013    (KR) .................. 10-2013-0132532

(51) Int. Cl.
*G01N 21/17* (2006.01)
*A61B 5/00* (2006.01)
*A61B 8/00* (2006.01)

(52) U.S. Cl.
CPC ....... *G01N 21/1702* (2013.01); *A61B 5/0062* (2013.01); *A61B 5/0095* (2013.01);
(Continued)

(58) Field of Classification Search
CPC ....... G01N 21/1702; G01N 2021/1704; G01N 2021/1706; G01N 2021/1708;
(Continued)

(56) References Cited

U.S. PATENT DOCUMENTS 6,106,471 A   8/2000   Wiesauer et al.
6,979,292 B2  12/2005  Kanayama et al.
(Continued)

FOREIGN PATENT DOCUMENTS

EP      2744053 A1    6/2014
JP   2010-022812 A    2/2010
(Continued)

OTHER PUBLICATIONS

Extended European Search Report issued in European Application No. 14168959.6 dated Mar. 11, 2015.
(Continued)

*Primary Examiner* — Paul West
*Assistant Examiner* — Xin Zhong
(74) *Attorney, Agent, or Firm* — McDermott Will & Emery LLP

(57) ABSTRACT

Provided are a photoacoustic apparatus and method of operating the same. The photoacoustic apparatus includes: a laser module that generates laser light and transmits a laser state signal indicating a state of a laser module; a probe including an optical output unit for irradiating laser light generated by the laser module onto an object and a scanner for detecting a photoacoustic signal that is generated from the object; a scanner controller for controlling a position of the scanner; a sequence controller for controlling acquisition of the photoacoustic signal based on the laser state signal; a signal receiver that is controlled by the sequence controller to acquire the photoacoustic signal; and a photoacoustic image generator for generating a photoacoustic image based
(Continued)

on the photoacoustic signal. The laser state signal includes a lasing ready state signal and a laser exposure state signal.

17 Claims, 8 Drawing Sheets

(52) U.S. Cl.
CPC .............. *A61B 8/44* (2013.01); *A61B 8/4427* (2013.01); *G01N 2201/06113* (2013.01); *G01N 2201/106* (2013.01)

(58) Field of Classification Search
CPC .... G01N 2201/06113; G01N 2201/106; A61B 8/44; A61B 5/0095; A61B 5/0062; A61B 8/4427; A61B 5/0093
See application file for complete search history.

(56) References Cited

U.S. PATENT DOCUMENTS

| | | | |
|---|---|---|---|
| 2007/0299341 A1* | 12/2007 | Wang | A61B 5/0091 600/443 |
| 2010/0094561 A1 | 4/2010 | Masumura | |
| 2010/0245766 A1* | 9/2010 | Zhang | A61B 5/0059 351/206 |
| 2010/0324422 A1 | 12/2010 | Wanda et al. | |
| 2011/0201914 A1* | 8/2011 | Wang | A61B 5/0059 600/407 |
| 2011/0224532 A1 | 9/2011 | Tanabe | |
| 2012/0302864 A1 | 11/2012 | Yoda | |
| 2013/0116539 A1* | 5/2013 | Nagao | A61B 5/0095 600/407 |
| 2014/0148660 A1 | 5/2014 | Irisawa et al. | |

FOREIGN PATENT DOCUMENTS

| | | |
|---|---|---|
| JP | 2010-116419 A | 5/2010 |
| JP | 2010-259604 A | 11/2010 |
| KR | 10-2014-0059466 A | 5/2014 |
| WO | 2011/091423 A2 | 7/2011 |
| WO | 2013/018634 A1 | 2/2013 |

OTHER PUBLICATIONS

Notice of Allowance issued in Korean Application No. 10-2013-0132532 dated Jan. 5, 2015, with English translation.

* cited by examiner

PHOTOACOUSTIC APPARATUS AND METHOD OF OPERATING THE SAME

RELATED APPLICATIONS

This application claims the benefit of Korean Patent Application No. 10-2013-0132532, filed on Nov. 1, 2013, in the Korean Intellectual Property Office, the disclosure of which is incorporated herein in its entirety by reference.

BACKGROUND

1. Field

One or more embodiments of the present invention relate to a photoacoustic apparatus and a method of operating the same, and more particularly, to a photoacoustic apparatus and method of operating the same that are capable of efficiently acquiring a photoacoustic image based on a signal indicating a state of a laser.

2. Description of the Related Art

A photoacoustic apparatus is capable of irradiating an object with light generated by a laser, receiving a photoacoustic signal generated from a matter in an object that absorbs light at a laser wavelength, and obtaining an image of an inner part of the object.

A conventional ultrasound diagnostic equipment transmits an ultrasound signal generated by a transducer in a probe to an object and receives information about an echo signal reflected from the object to image a bio-anatomical structure such as a position and a shape of a target within the object or bio-mechanical properties.

On the other hand, a photoacoustic apparatus may be used to measure a difference in chemical composition of a target object and optical properties thereof.

SUMMARY

One or more embodiments of the present invention include a photoacoustic apparatus and a method of operating the same that are capable of accurately acquiring a photoacoustic image by receiving a photoacoustic signal based on a signal indicating a state of a laser.

Additional aspects will be set forth in part in the description which follows and, in part, will be apparent from the description, or may be learned by practice of the presented embodiments.

According to one or more embodiments of the present invention, a photoacoustic apparatus includes: a laser module that generates laser light and transmits a laser state signal indicating a state of the laser module; a probe including an optical output unit for irradiating laser light generated by the laser module onto an object and a scanner for detecting a photoacoustic signal that is generated from the object; a scanner controller for controlling a position of the scanner; a sequence controller for controlling acquisition of the photoacoustic signal based on the laser state signal; a signal receiver that is controlled by the sequence controller to acquire the photoacoustic signal; and a photoacoustic image generator for generating a photoacoustic image based on the photoacoustic signal, wherein the laser state signal includes a lasing ready state signal and a laser exposure state signal.

When the laser state signal may be the laser exposure state signal, the sequence controller controls acquisition of the photoacoustic signal.

The scanner controller may control the position of the scanner based on the laser state signal.

When the laser state signal is the lasing ready state signal, the scanner controller may change the position of the scanner by a predetermined angle or a predetermined distance, and transmits information about the changed position of the scanner to the sequence controller.

The scanner controller may control the position of the scanner based on a preset scanning speed.

The sequence controller may acquire position information of the scanner based on the laser state signal.

When the laser state signal is the lasing ready state signal or the laser exposure state signal, the sequence controller may acquire the position information of the scanner.

The sequence controller may enter one of an ultrasound measurement mode and a photoacoustic measurement mode based on the laser state signal.

When the laser state signal is the lasing ready state signal, the sequence controller may enter the photoacoustic measurement mode.

The probe may further include a position sensor for acquiring position information of the scanner.

The apparatus may further include a display unit for displaying the photoacoustic image.

According to one or more embodiments of the present invention, a method of operating a photoacoustic apparatus includes: initializing a scanner for detecting a photoacoustic signal that is generated from an object; changing a position of the scanner; acquiring position information of the scanner; generating laser light and irradiating the laser light onto the object; acquiring a photoacoustic signal based on a laser state signal indicating a state of the laser module; and generating a photoacoustic image based on the photoacoustic signal, wherein the laser state signal includes a lasing ready state signal and a laser exposure state signal.

In the acquiring of the photoacoustic signal, the acquiring of the photoacoustic signal may be controlled when the laser state signal is the laser exposure state signal.

In the changing of the position of the scanner, the position of the scanner may be changed based on the laser state signal.

In the changing of the position of the scanner, the position of the scanner may be changed by a predetermined angle or a predetermined distance when the laser state signal is the lasing ready state signal.

In the changing of the position of the scanner, the position of the scanner may be changed based on a preset scanning speed.

In the acquiring of the position information of the scanner, the position information of the scanner may be acquired based on the laser state signal.

In the acquiring of the position information of the scanner, the position information of the scanner may be acquired when the laser state signal is the lasing ready state signal or the laser exposure state signal.

The method may further include entering one of an ultrasound measurement mode and a photoacoustic measurement mode based on the laser state signal.

In the entering of one of the ultrasound measurement mode and the photoacoustic measurement mode, the photoacoustic measurement mode may be entered when the laser state signal is the lasing ready state signal.

The method may further include displaying the generated photoacoustic image.

BRIEF DESCRIPTION OF THE DRAWINGS

These and/or other aspects will become apparent and more readily appreciated from the following description of the embodiments, taken in conjunction with the accompanying drawings, and reference numerals therein denote structural elements, in which.

DETAILED DESCRIPTION

Figure 1:
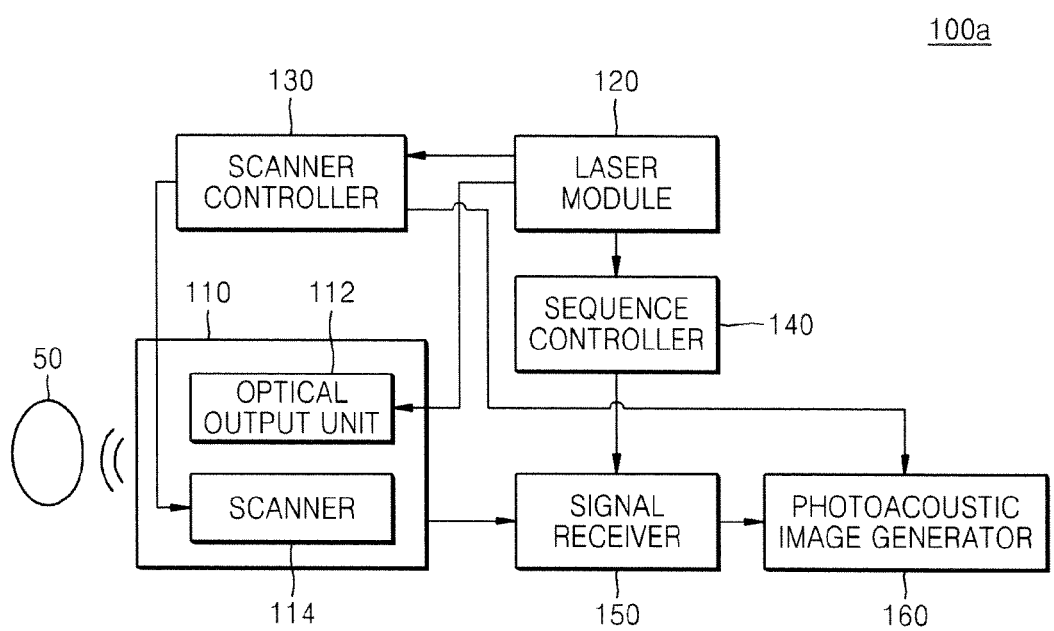
FIG. 1 is a block diagram of a configuration of a photoacoustic apparatus according to an exemplary embodiment of the present invention.

The terms used in this specification are those general terms currently widely used in the art in consideration of functions in regard to the present invention, but the terms may vary according to the intention of those of ordinary skill in the art, precedents, or new technology in the art. Also, specified terms may be selected by the applicant, and in this case, the detailed meaning thereof will be described in the detailed description of the invention. Thus, the terms used in the specification should be understood not as simple names but based on the meaning of the terms and the overall description of the invention.

Throughout the specification, it will also be understood that when a component "includes" an element, unless there is another opposite description thereto, it should be understood that the component does not exclude another element but may further include another element. In addition, terms such as " . . . unit", " . . . module", or the like refer to units that perform at least one function or operation, and the units may be implemented as hardware or software or as a combination of hardware and software. Expressions such as "at least one of," when preceding a list of elements, modify the entire list of elements and do not modify the individual elements of the list.

Throughout the specification, an "image" refers to an image of an object obtained by a photoacoustic apparatus. Furthermore, in the present specification, an "object" may include a person or an animal, or a part of a person or an animal. For example, the object may include organs such as the liver, the heart, the womb, the brain, a breast, and the abdomen, or a blood vessel. Furthermore, the "object" may include a phantom. The phantom means a material having a volume that is approximately equal to the density and effective atomic number of a living thing.

The image includes an ultrasound image and a photoacoustic image. The ultrasound image may be obtained based on an echo signal reflected from an object after an ultrasound wave has been transmitted to the object. The photoacoustic image may be acquired based on a photoacoustic signal that is received from an object irradiated with light (e.g., laser light).

The ultrasound image may be formed by using various imaging modes. For example, the ultrasound image may be at least one of an amplitude (A) mode image, a brightness (B) mode image, a color (C) mode image, and a Doppler (D) mode image.

According to an embodiment of the present invention, the may be a two-dimensional (2D) or three-dimensional (3D) image.

Furthermore, in the present specification, a "user" refers to a medical professional, such as a doctor, a nurse, a medical laboratory technologist, and a medical imaging expert, and an engineer who repairs a medical apparatus, but the user is not limited thereto.

One or more embodiments of the present invention will now be described more fully with reference to the accompanying drawings so that those skilled in the art to which the present invention pertains can easily carry out the invention. The invention may, however, be embodied in many different forms and should not be construed as being limited to the embodiments set forth herein.

FIG. 1 is a block diagram of a configuration of a photoacoustic apparatus 100a according to an exemplary embodiment of the present invention. Referring to FIG. 1, the photoacoustic apparatus 100a according to the present embodiment includes a laser module 120, a probe 110, a scanner controller 130, a sequence controller 140, a signal receiver 150, and a photoacoustic image generator 160.

The photoacoustic apparatus 100a may be embodied not only as a cart type device, but also as a portable type. Examples of portable photoacoustic apparatus may include a PACS viewer, a smartphone, a laptop computer, a personal digital assistant (PDA), and a tablet PC. However, the present invention is not limited thereto.

The laser module 120 may generate laser light and transmit a signal indicating a state of a laser module 120 that operates to emit the laser light (hereinafter, referred to as a laser state signal) to the scanner controller 130 and the sequence controller 140. In this case, the laser state signal may include a lasing ready state signal and a laser exposure state signal.

In this case, the lasing ready state signal indicates a state in which the laser module 120 starts lasing and is ready to emit laser light, and the laser exposure state signal indicates a state in which laser light is emitted.

The probe 110 may include an optical output unit 112 and a scanner 114. The optical output unit 112 receives laser light produced by the laser module 120 and irradiates the laser light onto an object 50. The scanner 114 may receive a photoacoustic signal from the object 50. The probe 110 may be a hand-held probe.

The scanner 114 may include at least one driver. A driver may be a rotary or linear driver. The scanner 114 may also perform scanning along at least one axis according to its configuration and further include a position sensor for controlling a position of a driver and acquiring position information of the driver. For example, the position sensor may be a rotary encoder, a linear encoder, an optical sensor, a gyro sensor, a velocity sensor, or an accelerometer, but is not limited thereto.

If the scanner 114 includes a driver that changes its position at a predetermined angle over time, the scanner 114 may not include the position sensor. In other words, when the scanner 114 is able to recognize position information of the driver through a signal used to control the position of the driver, the scanner 114 may not include a separate position sensor.

The scanner controller 130 receives a laser state signal and controls a position of the scanner 114 according to the laser state signal. For example, when a laser is in a lasing ready state, the scanner controller 130 may change a position of the driver in the scanner 114 by a predetermined angle or distance.

The sequence controller 140 receives a laser state signal and controls the signal receiver 150 to acquire a photoacoustic signal according to the laser state signal. For example, when the laser module 120 is in a laser exposure state, the sequence controller 140 may control the signal receiver 150 to receive a photoacoustic signal.

The sequence controller 140 may also determine a measurement mode according to the laser state signal. For example, if the laser module 120 is in a lasing ready state, the sequence controller 140 may quit an ultrasound measurement mode and enter a photoacoustic measurement mode.

The signal receiver 150 generates photoacoustic data by processing echo signals received from the probe 110 and may include an amplifier, an analog-to-digital converter (ADC), a reception delaying unit, and a summing unit. The amplifier amplifies photoacoustic signals at each channel, and the ADC performs analog-to-digital conversion on the amplified photoacoustic signals. The reception delaying unit applies a delay time for determining reception directionality to the photoacoustic signals output from the ADC, and the summing unit generates photoacoustic data by summing the photoacoustic signals processed by the reception delaying unit.

The photoacoustic image generator 160 generates a photoacoustic image by performing scan conversion on the photoacoustic data produced by the signal receiver 150.

The photoacoustic image generator 160 may generate a 3D photoacoustic image by performing volume rendering on volume data and position information of the scanner 114 acquired by the scanner controller 130. Furthermore, the photoacoustic image generator 160 may display additional information in the photoacoustic image by using text or graphics. In addition, the generated photoacoustic image may be stored in the memory.

Figure 2:
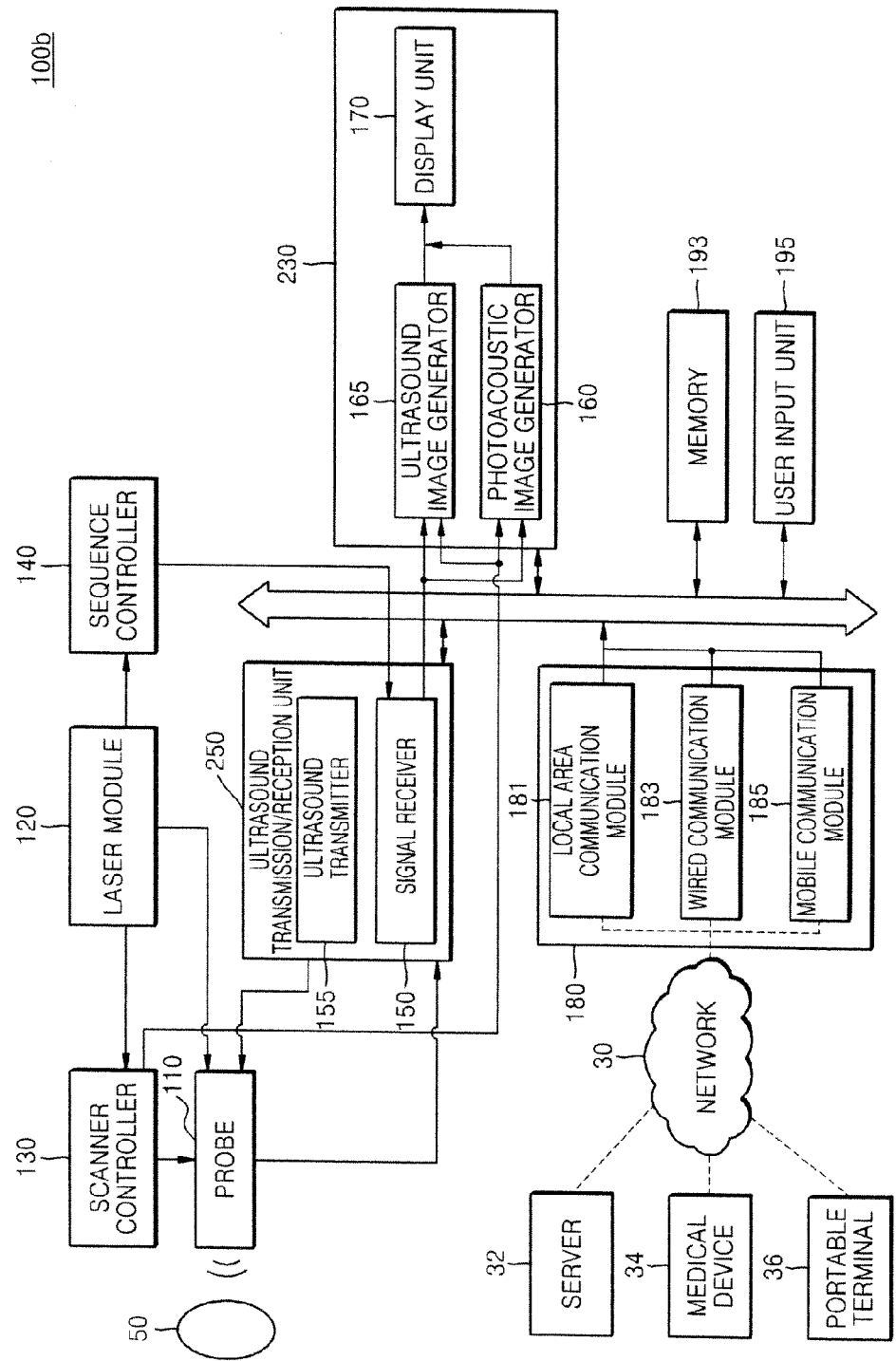
FIG. 2 is a block diagram of a configuration of a photoacoustic apparatus according to another exemplary embodiment of the present invention.

FIG. 2 is a block diagram of a configuration of a photoacoustic apparatus 100b according to another exemplary embodiment of the present invention. Referring to FIG. 2, the photoacoustic apparatus 100b according to the present embodiment includes a laser module 120, a probe 110, a scanner controller 130, a sequence controller 140, an ultrasound transmission/reception unit 250, an image processing unit 230, a communication unit 180, a memory 193, and a user input unit 195. The image processing unit 230 may include a photoacoustic image generator 160, an ultrasound image generator 165, and a display unit 170.

Since the laser module 120, the probe 110, the scanner controller 130, the sequence controller 140, the signal receiver 150, and the photoacoustic image generator 160 shown in FIG. 2 have the same configurations as those of their counterparts shown in FIG. 1, the descriptions thereof with reference to FIG. 1 apply to descriptions thereof with reference to FIG. 2.

The probe 110 may transmit ultrasound signals to an object 50 based on a driving signal that is applied by the ultrasound transmission/reception unit 250 and receive echo signals reflected from the object 50. The probe 110 includes a plurality of transducers that oscillate based on electrical signals transmitted thereto and generate acoustic energy, i.e., ultrasound waves. The probe 110 may also be connected to a main body of the photoacoustic apparatus 100b by wires or wirelessly. According to embodiments of the present invention, the photoacoustic apparatus 100b may include a plurality of probes 110.

An ultrasound transmitter 155 supplies a driving signal to the probe 110 and may include a pulse generator, a transmission delaying unit, and a pulser. The pulse generator generates pulses for forming transmission ultrasound waves based on a predetermined pulse repetition frequency (PRF), and the transmission delaying unit applies a delay time for determining transmission directionality to the pulses. The pulses to which the delay time is applied correspond to a plurality of piezoelectric vibrators included in the probe 110, respectively. The pulser applies a driving signal (or a driving pulse) to the probe 110 at a timing corresponding to each pulse to which a delay time is applied.

The signal receiver 150 may receive echo signals as well as photoacoustic signals, and include an amplifier, an ADC, a reception delaying unit, and a summing unit. The amplifier may amplify echo signals at each channel, and the ADC may perform analog-to-digital conversion on the amplified echo signals. The reception delaying unit may apply a delay time for determining reception directionality to the echo signals output from the ADC, and the summing unit generates ultrasound data by summing the echo signals processed by the reception delaying unit.

The ultrasound image generator 165 generates an ultrasound image. An ultrasound image may include not only a grayscale ultrasound image obtained by scanning an object in an A mode, a B mode, and a motion (M) mode, but also a Doppler image showing movement of an object. The Doppler image may include a blood flow Doppler image (also called a color Doppler image) showing a flow of blood, a tissue Doppler image showing movement of tissue, and a spectral Doppler image showing moving speed of an object as a waveform. The ultrasound image generator 165 may also produce a 3D image by performing volume rendering on volume data and position information of a scanner acquired by the scanner controller 130.

The ultrasound image generator 165 may include a B-mode processor and a Doppler processor. The B mode processor may extract B mode components from ultrasound data and process the B mode components. The ultrasound image generator 165 may generate an ultrasound image indicating signal intensities as brightness based on the extracted B mode components.

Similarly, the Doppler processor may extract Doppler components from ultrasound data, and the ultrasound image generator 165 may generate a Doppler image indicating movement of an object as colors or waveforms based on the extracted Doppler components.

The display unit 170 may display and output an image produced by the photoacoustic image generator 160 or the ultrasound image generator 165. The display unit 170 may display an ultrasound image as well as various information processed by the photoacoustic apparatus 100b on a screen via a graphic user interlace (GUI). Meanwhile, the photoacoustic apparatus 100b may include two or more display units 170 according to embodiments of the present invention.

The display unit 170 may include at least one of a liquid crystal display (LCD), a thin-film transistor-LCD (TFT-LCD), an organic light-emitting diode (OLED), a flexible display, a 3D display, and an electrophoretic display.

Furthermore, when the display unit 170 forms a cross-layer structure with the user input unit 195, the display unit 170 may be used as both an output device and an input device capable of inputting information when a user touches it.

The communication unit 180 is connected to a network 30 by wires or wirelessly and communicates with an external device or a server. The communication unit 180 may exchange data with a hospital server or another medical device in a hospital that is connected through a picture archiving and communications system (PACS). Furthermore, the communication unit 180 may perform data communication according to the digital imaging and communications in medicine (DICOM) standard.

The communication unit 180 may transmit or receive data related to diagnosis of an object, e.g., an ultrasound image, a photoacoustic image, ultrasound data, and Doppler data of the object, via the network 30. The communication unit 180 may also transmit or receive medical images obtained from other medical imaging devices such as a computed tomography (CT) apparatus, a magnetic resonance imaging (MRI) apparatus, and an X-ray apparatus. Furthermore, the communication unit 180 may receive information related to a diagnosis history or treatment schedule of a patient from a server and utilize the information for diagnosing the patient. Furthermore, the communication unit 180 may perform data communication not only with a server or a medical device in a hospital, but also with a portable terminal of a doctor or a patient.

The communication unit 180 may be connected to the network 30 by wires or wirelessly to exchange data with a server 32, a medical device 34, or a portable terminal 36. The communication unit 180 may include one or more components that enable communication with external devices, e.g., a local area communication module 181, a wired communication module 183, and a mobile communication module 185.

The local area communication module 181 may refer to a module for local area communication within a predetermined distance. Examples of local area communication techniques according to an embodiment of the present invention may include wireless Local Area Network (LAN), Wireless Fidelity (Wi-Fi), Bluetooth, ZigBee, Wi-Fi Direct (WFD), Ultra Wideband (UWB), Infrared Data Association (IrDA), Bluetooth Low Energy (BLE), and Near Field Communication (NFC). However, the present invention is not limited thereto.

The wired communication module 183 refers to a module for communication using electric signals or optical signals. Examples of wired communication techniques according to an embodiment of the present invention may include wired communication techniques using a pair cable, a coaxial cable, an optical fiber cable, and an Ethernet cable.

The mobile communication module 185 transmits or receives wireless signals to or from at least one of a base station, an external terminal, and a server on a mobile communication network. Here, the wireless signals may include voice call signals, video call signals, or various types of data for transmission and reception of text/multimedia messages.

The memory 193 stores various information that is processed by the photoacoustic apparatus 100b. For example, the memory 193 may store medical data related to diagnosis of an object, such as ultrasound data and an ultrasound image that are input or output, as well as algorithms or programs that are executed in the photoacoustic apparatus 100b.

The memory 193 may be implemented as various types of storage media such as a flash memory, a hard disk drive, an Electrically Erasable Programmable Read-Only Memory (EEPROM), etc. Furthermore, the photoacoustic apparatus 100b may utilize a web storage or a cloud server that performs a storage function of the memory 193 online The user input unit 195 refers to a means via which a user inputs data for controlling the photoacoustic apparatus 100b. The user input unit 195 may include hardware components, such as a keypad, a mouse, a touch pad, a trackball, and a jog switch. However, the present invention is not limited thereto, and the user input unit 195 may further include various other input means including an electrocardiogram measuring module, a respiration measuring module, a voice recognition sensor, a gesture recognition sensor, a fingerprint recognition sensor, an iris recognition sensor, a depth sensor, a distance sensor, etc.

All or some of the probe 110, the ultrasound transmitter 155, the signal receiver 150, the ultrasound image generator 165, the photoacoustic image generator 160, the sequence controller 140, the scanner controller 130, the communication unit 180, the memory 193, and the user input unit 195 may be operated by software modules. However, the present invention is not limited thereto, and some of the components stated above may be operated by hardware modules.

The block diagrams of the photoacoustic apparatuses 100a and 100b of FIGS. 1 and 2 are provided as embodiments of the present invention. Thus, each of the components illustrated in the block diagrams may be integrated, added, or omitted according to the specification for a photoacoustic apparatus implemented actually. In other words, two or more components may be integrated into a signal component, or one component may be segmented into two or more components when necessary. Functions performed by each block are considered for describing the embodiments of the present invention, and detailed operations and components thereof do not limit the scope of the present invention.

Figure 3:
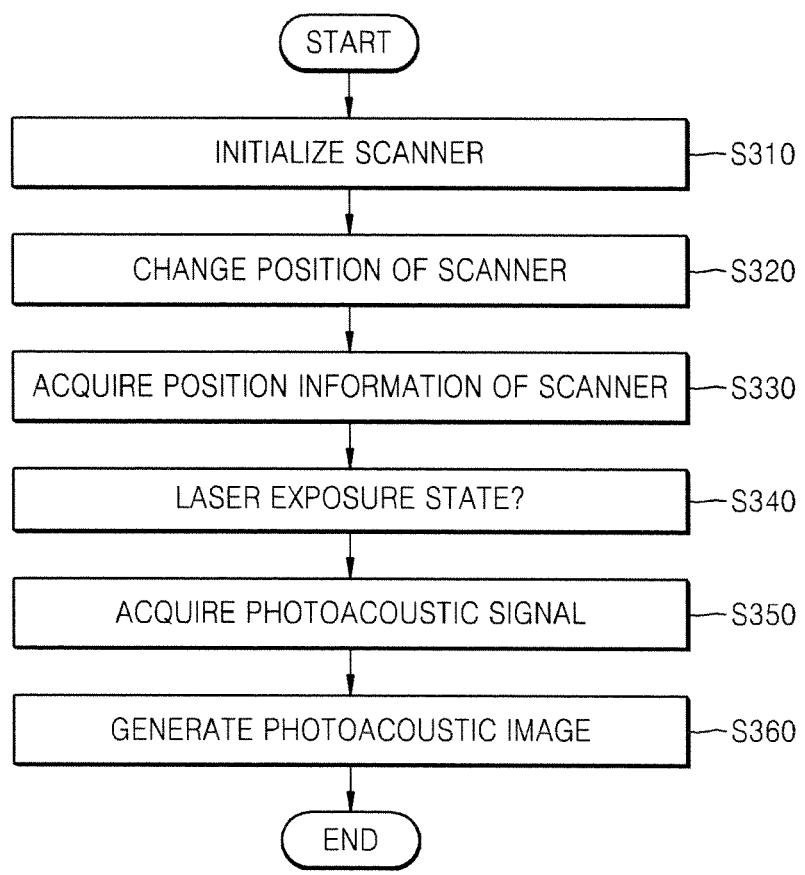
FIG. 3 is a flowchart of a method of operating a photoacoustic apparatus while in an asynchronous mode.

FIG. 3 is a flowchart of a method of operating the photoacoustic apparatus 100a or 100b while in an asynchronous mode, according to an exemplary embodiment of the present invention.

Referring to FIGS. 1 through 3, the photoacoustic apparatus 100a or 100b may initialize the scanner 114 (S310). For example, if a user starts a photoacoustic measurement, the sequence controller 140 may transmit an initialization command to the scanner controller 130. Upon receipt of the initialization command, the scanner controller 130 may control initialization of position information of a driver included in the scanner 114.

When the initialization is completed, the scanner controller 130 may transmit an initialization completion signal to the sequence controller 140. After receiving the initialization completion signal, the sequence controller 140 may set parameters for photoacoustic measurement.

The photoacoustic apparatus 100a or 100b may change a position of the scanner 114 (S320). For example, the photoacoustic apparatus 100a or 100b may continue to change the position of the scanner 114 by changing a position of the driver by a predetermined angle or distance according to a preset scanning speed of the scanner 114.

The photoacoustic apparatus 100a or 100b may acquire position information of the scanner 114 (S330). The position information of the scanner 114 may be obtained through a position sensor included in the scanner 114. Alternatively, when the scanner 114 includes a driver whose position changes by a predetermined angle over time, the photoacoustic apparatus 100a or 100b may obtain position information of the scanner 114 based on information about the time and the angle.

In this case, the photoacoustic apparatus 100a or 100b may acquire position information of the scanner 114 when a laser is in a lasing ready state or in a laser exposure state. However, the present invention is not limited thereto.

The photoacoustic apparatus 100a or 100b may determine whether the laser is in a laser exposure state (S340) and acquire a photoacoustic signal if the laser is in the laser exposure state (S350).

For example, if the laser module 120 transmits a lasing ready state signal to the sequence controller 140, the sequence controller 140 may enter a photoacoustic measurement mode and then wait for the laser module 120 to generate a laser exposure state signal.

The laser module 120 transmits a laser exposure state signal to the sequence controller 140 and the scanner controller 130 as it emits laser light. The scanner controller 130 receives the laser exposure state signal and transmits position information of the scanner 114 to the sequence controller 140. Upon detection of a lasing ready state signal generated by the laser module 120, the scanner controller 130 may transmit the position information of the scanner 114 to the sequence controller 140 according to a mutual regulation designed between the scanner controller 130 and the sequence controller 140. The sequence controller 140 receives a laser exposure state signal and controls the signal receiver 150 to acquire a photoacoustic signal. Thereby, the signal receiver 150 may acquire a photoacoustic signal generated from the object 50.

The photoacoustic apparatus 100a or 100b may create a photoacoustic image based on the acquired photoacoustic signal (S360). In this case, the photoacoustic apparatus 100a or 100b may generate volume data for the photoacoustic signal by using the position information of the scanner 114 obtained from the scanner controller 130 and performing scan conversion on photoacoustic data. The photoacoustic apparatus 100a or 100b may also create a 3D image by performing volume rendering on the volume data.

Figure 4:
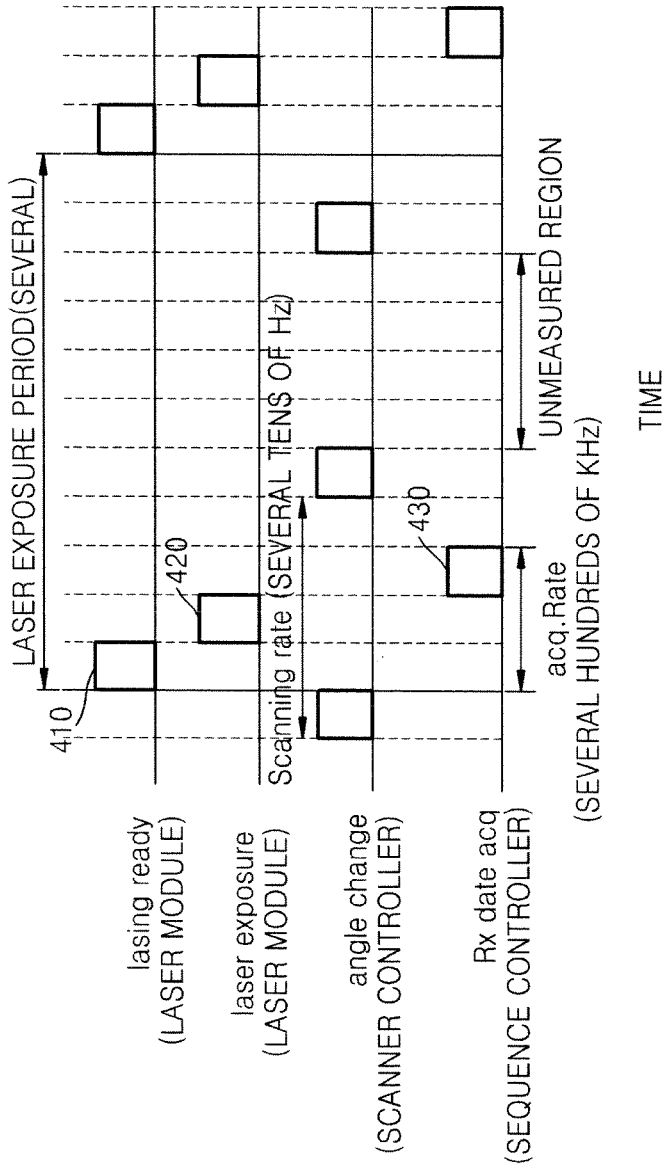
FIG. 4 is a timing diagram for the operation of the photoacoustic apparatus in an asynchronous mode illustrated in FIG. 3.

FIG. 4 is a timing diagram for the operation of the photoacoustic apparatus 100a or 100b in an asynchronous mode illustrated in FIG. 3.

Referring to FIG. 4, the scanner controller 130 may change a position of the scanner 114 based on a preset scanning speed, regardless of a laser state signal. In this case, the preset scanning speed may be several tens of Hz, but is not limited thereto.

The laser module 120 may first output a lasing ready state signal (410) and then a laser exposure state signal as it emits laser light (420). The sequence controller 140 that has received the laser exposure state signal may control acquisition of the photoacoustic signal (430).

Furthermore, when the sequence controller 140 acquires position information of the scanner 114 upon generation of a lasing ready state signal among laser state signals, as shown in FIG. 4, a period of a laser state signal may be adjusted so that a sequence from generation of a lasing ready state signal to acquisition of a photoacoustic signal may be set to have a period of several hundreds of KHz. In this case, even when the operation of a driver having a bandwidth of several hundreds of Hz collides with the sequence, a photoacoustic signal may be acquired during a change in a position of the driver since the speed of acquisition of the photoacoustic signal is more than 1000 times higher than the speed of the driver. Thus, possible position errors in a measured image may be ignored.

Furthermore, as shown in FIG. 4, if a laser exposure period between generation of a current lasing ready state signal and generation of a next lasing ready state signal is several Hz and the scanning speed is several tens of Hz, a region (unmeasured region) where a photoacoustic signal is not acquired may occur because the scanning speed is faster than the laser exposure period. Images for the unmeasured region may be processed using an interpolation technique.

Figure 5:
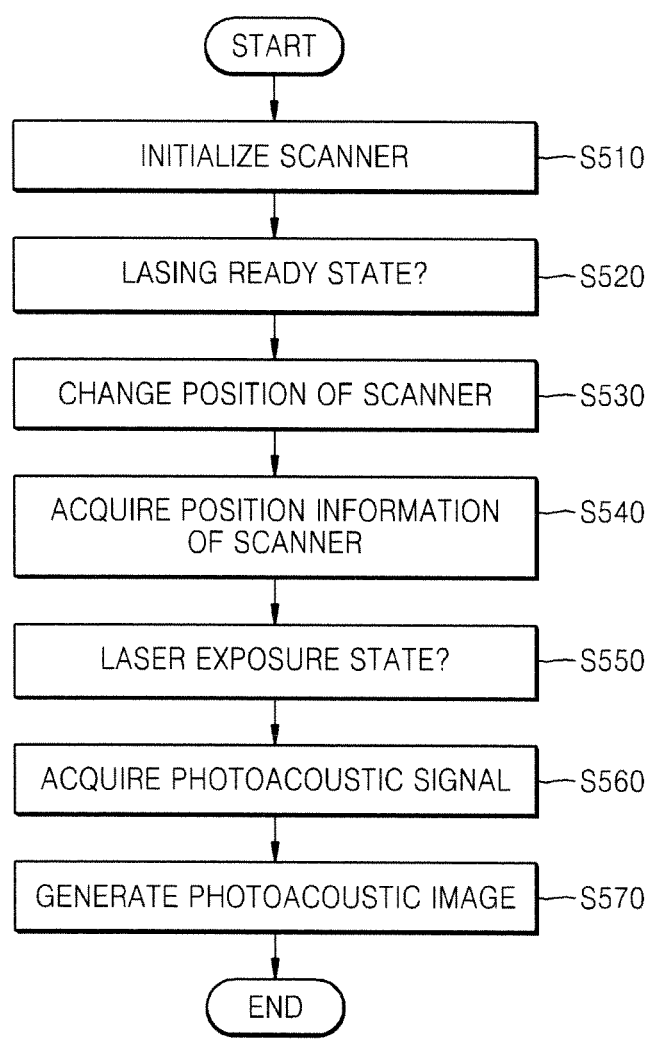
FIG. 5 is a flowchart of a method of operating a photoacoustic apparatus while in a synchronous mode, according to an exemplary embodiment of the present invention.

FIG. 5 is a flowchart of a method of operating the photoacoustic apparatus 100a or 100b while in a synchronous mode, according to an exemplary embodiment of the present invention.

Referring to FIGS. 1, 2, and 5, the photoacoustic apparatus 100a or 100b may initialize the scanner 114 (S510). For example, if a user starts a photoacoustic measurement, the sequence controller 140 may transmit an initialization command to the scanner controller 130. Upon receipt of the initialization command, the scanner controller 130 may control initialization of position information of a driver included in the scanner 114.

When the initialization is completed, the scanner controller 130 may transmit an initialization completion signal to the sequence controller 140. After receiving the initialization completion signal, the sequence controller 140 may set parameters for photoacoustic measurement.

Upon receipt of a lasing ready state signal from the laser module 120 (S520), the scanner controller 130 may change a position of the scanner 114 (S530). For example, the scanner controller 130 may change the position of the scanner 114 by changing a position of the driver in the scanner 114 by a predetermined angle or distance.

If the position of the scanner 114 is changed, the photoacoustic apparatus 100a or 100b may acquire position information of the scanner 114 (S540). For example, the scanner controller 130 may transmit the position information of the scanner 114 that is acquired by a position sensor in the scanner 114 to the sequence controller 140.

The scanner controller 130 may also wait for receiving a next lasing ready state signal.

The photoacoustic apparatus 100a or 100b may determine whether a laser module 120 is in a laser exposure state (S550) and acquire a photoacoustic signal if the laser module 120 is in the laser exposure state (S560).

For example, the laser module 120 may transmit a laser exposure state signal to the sequence controller 140 as it emits laser light. The sequence controller 140 may receive the laser exposure state signal and control the signal receiver 150 so as to enter a photoacoustic measurement mode. Thereby, the signal receiver 150 may acquire a photoacoustic signal generated from the object 50.

The photoacoustic apparatus 100a or 100b may create a photoacoustic image based on the acquired photoacoustic signal (S570). In this case, the photoacoustic apparatus 100a or 100b may generate volume data for the photoacoustic signal by using the position information of the scanner 114 obtained from the scanner controller 130 and performing scan conversion on photoacoustic data. The photoacoustic apparatus 100a or 100b may also create a 3D image by performing volume rendering on the volume data.

Figure 6:
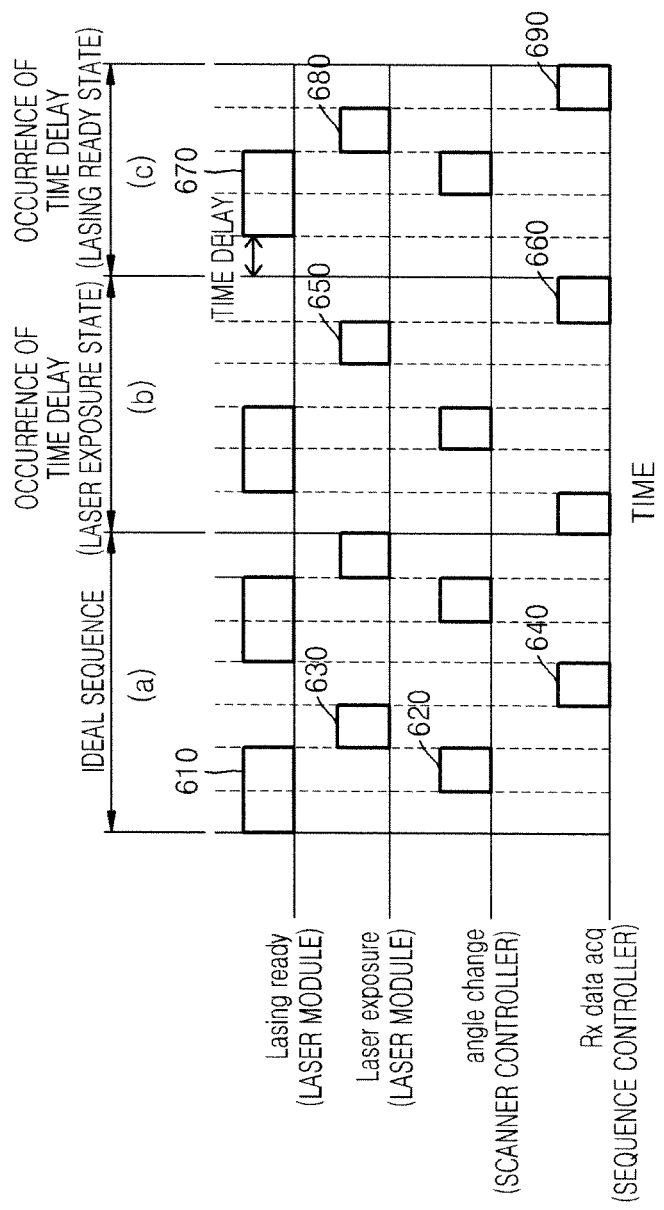
FIG. 6 is a timing diagram for the operation of the photoacoustic apparatus in a synchronous mode illustrated in FIG. 5.

FIG. 6 is a timing diagram for the operation of the photoacoustic apparatus 100a or 100b in a synchronous mode illustrated in FIG. 5.

FIG. 6 illustrates timing block diagrams for an ideal sequence (a) having no time delay, a sequence (b) having a time delay in the exposure of laser light from the laser module 120, and a sequence (c) having a time delay introduced by the laser module 120 being ready for lasing.

Referring to the timing block diagram for the ideal sequence (a), the laser module 120 outputs a lasing ready state signal (610). Upon receipt of the lasing ready state signal, the scanner controller 130 may change a position of the scanner 114 (620).

After outputting the lasing ready state signal, the laser module 120 may output a laser exposure state signal (630). Upon receipt of the laser exposure state signal, the sequence controller 140 may control acquisition of a photoacoustic signal (640).

The time during which a laser state signal output from the laser module 120 is in an active state may be set in consideration of the time during which the driver performs driving.

For example, as shown in FIG. 6, by increasing the duration of a lasing ready state signal, the photoacoustic apparatus 100a or 100b may set the time during which a laser state signal remains active so that the time during which the driver performs driving may end before a laser exposure state signal is output.

Referring to the timing block diagram for the sequence (b), the laser module 120 outputs a lasing ready state signal. Upon receipt of the lasing ready state signal, the scanner controller 130 may change a position of the scanner 114.

After outputting the lasing ready state signal, the laser module 120 may output a laser exposure state signal. In this case, a time delay occurs in the emission of laser light (650). For example, the time delay may be introduced due to a temperature of an area surrounding the laser module 120 or a lasing state.

The sequence controller 140 receives a laser exposure state signal to control acquisition of a photoacoustic signal (660).

Referring to the timing block diagram for the ideal sequence (c), the laser module 120 outputs a lasing ready state signal. In this case, a time delay occurs in being ready for lasing (670). For example, the time delay may be introduced due to a temperature of an area surrounding the laser module 120 or a lasing state.

Upon receipt of the lasing ready state signal, the scanner controller 130 may change a position of the scanner 114.

After outputting the lasing ready state signal, the laser module 120 may output a laser exposure state signal (680). Upon receipt of the laser exposure state signal, the sequence controller 140 may control acquisition of a photoacoustic signal (690).

Thus, as evident from FIG. 6, even when the time delay occurs in the emission of laser light or in being ready for lasing, a collision may not occur between the sequences (b) and (c).

In other words, since points in time when the position of the scanner 114 is changed, when the position of the scanner 114 is acquired, and when a photoacoustic signal is acquired are synchronized to corresponding laser states, such a collision does not occur between sequences even if a time delay are introduced in generation of a lasing ready state signal or laser exposure state signal. Thus, the photoacoustic apparatus 100a or 100b may efficiently acquire a photoacoustic signal.

Figure 7:
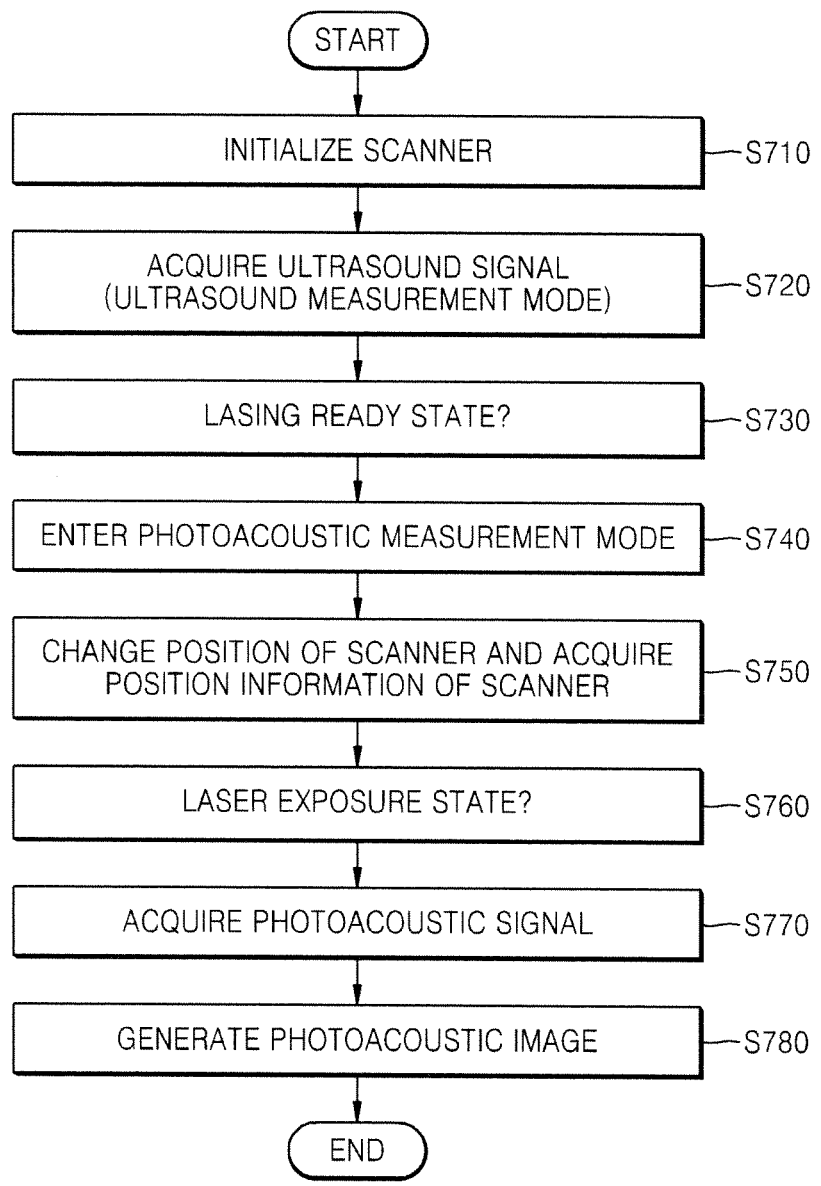
FIG. 7 is a flowchart of a method of operating a photoacoustic apparatus while in a synchronous simultaneous mode, according to an exemplary embodiment of the present invention.

FIG. 7 is a flowchart of a method of operating the photoacoustic apparatus 100a or 100b while in a synchronized simultaneous mode, according to an exemplary embodiment of the present invention.

Referring to FIGS. 1, 2, and 7, the photoacoustic apparatus 100a or 100b may initialize the scanner 114 (S710). For example, if a user starts a photoacoustic measurement, the sequence controller 140 may transmit an initialization command to the scanner controller 130. Upon receipt of the initialization command, the scanner controller 130 may control initialization of position information of a driver included in the scanner 114.

When the initialization is completed, the scanner controller 130 may transmit an initialization completion signal to the sequence controller 140. After receiving the initialization completion signal, the sequence controller 140 may enter an ultrasound measurement mode and set parameters for ultrasound measurement.

The sequence controller 140 may also control the signal receiver 150 to acquire an ultrasound signal (S720). The signal receiver 150 may receive the ultrasound signal, and the ultrasound image generator 165 may generate an ultrasound image based on the received ultrasound signal. In this case, the ultrasound image may be a B mode ultrasound image.

The sequence controller 140 continues to maintain the ultrasound measurement mode until receiving a lasing ready state signal from the laser module 120.

The laser module 120 may transmit a lasing ready state signal to the scanner controller 130 and the sequence controller 140 (S730).

Upon receipt of the lasing ready state signal, the sequence controller 140 may enter a photoacoustic measurement mode (S740) and set parameters for photoacoustic measurement.

Upon receipt of the lasing ready state signal, the scanner controller 130 may change a position of the scanner 114. For example, the scanner controller 130 may change the position of the scanner 114 by changing a position of a driver in the scanner 114 by a predetermined angle or distance.

After the position of the scanner 114 is changed, the photoacoustic apparatus 100a or 100b may acquire position information of the scanner 114 (S750). For example, the scanner controller 130 may transmit the position information of the scanner 114 that is acquired by a position sensor in the scanner 114 to the sequence controller 140.

The scanner controller 130 may also wait for receiving a next lasing ready state signal.

The photoacoustic apparatus 100a or 100b may determine whether a laser is in a laser exposure state (S760) and acquire a photoacoustic signal if the laser is in the laser exposure state (S770).

For example, the laser module 120 may transmit a laser exposure state signal to the sequence controller 140 as it emits laser light. The sequence controller 140 may receive the laser exposure state signal and may control the signal receiver 150 to acquire a photoacoustic signal.

Thereby, the signal receiver 150 may receive the photoacoustic signal generated from the object 50, and the photoacoustic image generator 160 may create a photoacoustic image based on the received photoacoustic signal (S780).

In this case, the photoacoustic apparatus 100a or 100b may generate volume data for the photoacoustic signal by using the position information of the scanner 114 acquired by the scanner controller 130 and performing scan conversion on photoacoustic data. The photoacoustic apparatus 100a or 100b may also create a 3D image by performing volume rendering on the volume data.

Furthermore, the sequence controller 140 may return to the ultrasound measurement mode and control the signal receiver 150 to acquire an ultrasound signal, until receiving a next lasing ready state signal.

Figure 8:
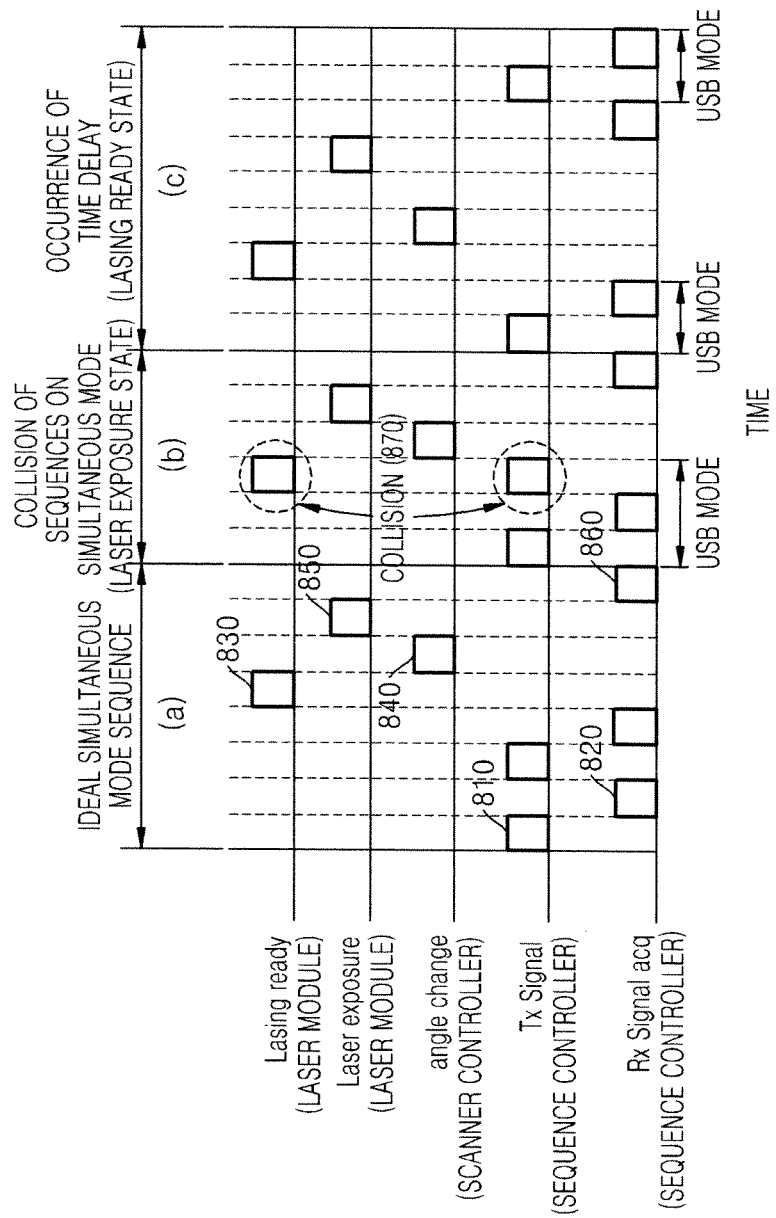
FIG. 8 is a timing diagram for the operation of the photoacoustic apparatus in a synchronous simultaneous mode illustrated in FIG. 7.

FIG. 8 is a timing diagram for the operation of the photoacoustic apparatus 100a or 100b in a synchronized simultaneous mode illustrated in FIG. 7.

FIG. 8 illustrates timing block diagrams for an ideal simultaneous mode sequence (a) having no time delay, a sequence (b) having a time shift in being ready for lasing, and a sequence (c) having a time delay in the emission of laser light.

Referring to the timing block diagram for the ideal simultaneous mode sequence (a), the sequence controller 140 may enter an ultrasound measurement mode and control the ultrasound transmitter 155 and the signal receiver 150 to transmit an ultrasound signal (810) and receive an echo signal reflected from the object 50 (820), respectively.

If the laser module 120 outputs a lasing ready state signal (830), the scanner controller 130 may receive the lasing ready state signal to change a position of the scanner 114 (840).

After outputting the lasing ready state signal, the laser module 120 may output a laser exposure state signal (850). Upon receipt of the laser exposure state signal, the sequence controller 140 may enter a photoacoustic measurement mode and control the signal receiver 150 to acquire a photoacoustic signal (860).

Referring to the timing block diagram for the sequence (b), in a simultaneous mode, acquisition of an ultrasound signal in an ultrasound measurement mode collides with a lasing ready state signal (870).

In this case, the photoacoustic apparatus 100a or 100b may suspend acquisition of the ultrasound signal and shift the ultrasound measurement mode to a photoacoustic measurement mode. Alternatively, the photoacoustic apparatus 100a or 100b may adjust a time interval between output of a lasing ready state signal and output of a laser exposure state signal so that the lasing ready state signal is output after acquisition of the ultrasound signal.

Referring to the timing block diagram for the sequence (c), since the sequence controller 140 is synchronized to a laser exposure state signal to control acquisition of the position of the scanner 114 and the photoacoustic signal, a collision does not occur between acquisition of the photoacoustic signal and execution of an ultrasound measurement mode even if a time delay occurs in generation of the laser exposure state signal. Thus, the user may efficiently acquire a photoacoustic signal.

A method of operating a photoacoustic apparatus according to an embodiment of the present invention may be embodied as a computer-readable code on a computer-readable storage medium. The computer-readable storage medium is any data storage device that can store data which can be thereafter read by a computer system. Examples of computer-readable storage media include ROM, random-access memory (RAM), CD-ROMs, magnetic tapes, floppy disks, and optical data storage devices. The computer-readable storage media can also be distributed over network coupled computer systems so that computer-readable codes are stored and executed in a distributed fashion.

It should be understood that the exemplary embodiments described therein should be considered in a descriptive sense only and not for purposes of limitation. While one or more embodiments of the present invention have been described with reference to the figures, it will be understood by those of ordinary skill in the art that various changes in form and details may be made therein without departing from the spirit and scope of the present invention as defined by the following claims. The modifications in embodiments of the present invention should not be understood independently of the technical idea or outlook of the present invention.

What is claimed is:

1. A photoacoustic apparatus comprising:
   a laser module that generates laser light and transmits a laser state signal indicating a state of the laser module, the laser state signal includes a lasing ready state signal and a laser exposure state signal;
   a probe including an optical output unit for irradiating laser light generated by the laser module onto an object and a scanner for detecting a photoacoustic signal that is generated from the object;
   a scanner controller for changing a position of the scanner;
   a sequence controller for controlling acquisition of the photoacoustic signal;
   a signal receiver that is controlled by the sequence controller to acquire the photoacoustic signal; and
   a photoacoustic image generator for generating a photoacoustic image based on the photoacoustic signal,
   wherein the laser module is configured to, in response to starting of lasing, transmit the lasing ready state signal to the scanner controller, and in response to laser light being emitted, transmit the laser exposure state signal to the sequence controller,
   wherein the scanner controller is configured to, in response to receiving the lasing ready state signal from the laser module, change the position of the scanner and transmit the changed position of the scanner to the sequence controller,
   wherein the sequence controller is configured to, in response to receiving the laser exposure state signal from the laser module, control the signal receiver to acquire the photoacoustic signal and control the photoacoustic image generator to generate the photoacoustic image based on the photoacoustic signal and the changed position of the scanner.

2. The apparatus of claim 1, wherein when the laser state signal is the lasing ready state signal, the scanner controller changes the position of the scanner by a predetermined angle or a predetermined distance, and transmits information about the changed position of the scanner to the sequence controller.

3. The apparatus of claim 1, wherein the scanner controller controls the position of the scanner based on a preset scanning speed.

4. The apparatus of claim 1, wherein the sequence controller acquires position information of the scanner based on the laser state signal.

5. The apparatus of claim 4, wherein when the laser state signal is the lasing ready state signal or the laser exposure state signal, the sequence controller acquires the position information of the scanner.

6. The apparatus of claim 1, wherein the sequence controller enters one of an ultrasound measurement mode and a photoacoustic measurement mode based on the laser state signal.

7. The apparatus of claim 6, wherein when the laser state signal is the lasing ready state signal, the sequence controller enters the photoacoustic measurement mode.

8. The apparatus of claim 1, wherein the probe further comprises a position sensor for acquiring position information of the scanner.

9. The apparatus of claim 1, further comprising a display unit for displaying the photoacoustic image.

10. The apparatus of claim 1, wherein the sequence controller is configured to control the signal receiver acquire an ultrasound signal from the object and in response to receiving the lasing ready state signal from the laser module, to control the signal receiver to acquire the photoacoustic signal.

11. A method of operating a photoacoustic apparatus, the method comprising:
  initializing a scanner for detecting a photoacoustic signal that is generated from an object;
  starting lasing by a laser module of the photoacoustic apparatus;
  in response to the starting of the lasing, transmitting a lasing ready state signal to a scanner controller of the photoacoustic apparatus, by the laser module;
  in response to receiving the lasing ready state signal, changing a position of the scanner by the scanner controller;
  transmitting the changed position of the scanner to a sequence controller of the photoacoustic apparatus;
  emitting laser light by the laser module of the photoacoustic apparatus;
  in response to the emitting of the laser light, transmitting a laser exposure state signal to the sequence controller of the photoacoustic apparatus, by the laser module of the photoacoustic apparatus;
  irradiating the laser light onto the object by a probe of the photoacoustic apparatus;
  in response to receiving the laser exposure state signal, acquiring the photoacoustic signal from the object; and
  generating a photoacoustic image based on the photoacoustic signal by the sequence controller.

12. The method of claim 11, wherein in the changing of the position of the scanner, the position of the scanner is changed by a predetermined angle or a predetermined distance.

13. The method of claim 11, wherein in the changing of the position of the scanner, the position of the scanner is changed based on a preset scanning speed.

14. The method of claim 11, further comprising entering one of an ultrasound measurement mode and a photoacoustic measurement mode.

15. The method of claim 14, wherein in the entering of one of the ultrasound measurement mode and the photoacoustic measurement mode, the photoacoustic measurement mode is entered, in response to receiving the lasing ready state signal by the sequence controller.

16. The method of claim 11, further comprising displaying the generated photoacoustic image.

17. A non-transitory computer-readable recording medium having recorded thereon a program for executing the method of claim 11 on a computer.

* * * * *